United States Patent
Takemoto et al.

(10) Patent No.: US 10,927,084 B2
(45) Date of Patent: Feb. 23, 2021

(54) ALKANOLAMINE, FRICTION-REDUCING AGENT, AND LUBRICATING OIL COMPOSITION

(71) Applicant: TOSOH CORPORATION, Shunan (JP)

(72) Inventors: Arimitsu Takemoto, Shunan (JP); Hiroshi Awano, Shunan (JP); Hisao Eguchi, Shunan (JP); Manabu Yanase, Shunan (JP)

(73) Assignee: TOSOH CORPORATION, Shunan (JP)

( * ) Notice: Subject to any disclaimer, the term of this patent is extended or adjusted under 35 U.S.C. 154(b) by 0 days.

(21) Appl. No.: 16/478,496

(22) PCT Filed: Jan. 18, 2018

(86) PCT No.: PCT/JP2018/001322
§ 371 (c)(1),
(2) Date: Jul. 17, 2019

(87) PCT Pub. No.: WO2018/139326
PCT Pub. Date: Aug. 2, 2018

(65) Prior Publication Data
US 2020/0039942 A1    Feb. 6, 2020

(30) Foreign Application Priority Data
Jan. 26, 2017 (JP) .............................. JP2017-012379
Jun. 13, 2017 (JP) .............................. JP2017-115863

(51) Int. Cl.
| | | |
|---|---|---|
| C07D 241/04 | (2006.01) | |
| C10M 125/10 | (2006.01) | |
| C10M 133/40 | (2006.01) | |
| C10M 137/10 | (2006.01) | |
| C10M 139/00 | (2006.01) | |
| C10M 141/12 | (2006.01) | |

(52) U.S. Cl.
CPC ......... *C07D 241/04* (2013.01); *C10M 125/10* (2013.01); *C10M 133/40* (2013.01); *C10M 137/10* (2013.01); *C10M 139/00* (2013.01); *C10M 141/12* (2013.01); *C10M 2201/062* (2013.01); *C10M 2201/08* (2013.01); *C10M 2215/221* (2013.01); *C10M 2223/045* (2013.01); *C10M 2227/00* (2013.01)

(58) Field of Classification Search
CPC ............. C07D 241/04; C07D 295/088; C10M 125/10; C10M 133/10; C10M 133/40; C10M 137/10; C10M 139/00; C10M 141/06; C10M 141/12; C10M 2201/08; C10M 2215/221; C10M 2223/045; C10M 2227/00
See application file for complete search history.

(56) References Cited

U.S. PATENT DOCUMENTS

| | | | |
|---|---|---|---|
| 3,163,649 A * | 12/1964 | Morren ............. | C07D 295/088 544/394 |
| 3,173,917 A * | 3/1965 | Starker ............... | C07D 295/02 544/392 |
| 3,673,186 A * | 6/1972 | Cyba ................... | C07D 239/04 544/401 |
| 3,872,171 A | 3/1975 | Cronin et al. | |
| 4,034,040 A | 7/1977 | Cronin et al. | |
| 4,087,552 A | 5/1978 | Cronin et al. | |

(Continued)

FOREIGN PATENT DOCUMENTS

| | | |
|---|---|---|
| GB | 834300 | 5/1960 |
| JP | 56-150068 | 11/1981 |

(Continued)

OTHER PUBLICATIONS

International Preliminary Report on Patentability issued in PCT/JP2018/001322 dated Jul 30, 2019.
International Search Report issued in PCT/JP2018/001322 dated Apr. 3, 2018.
Fiedler et al., "Surface Chemical Characterization of Maleic Acid Mono[2-(4-alkylpiperazinyl)ethyl esters]. 1. The Complex Adsorption Behavior of an Ampholytic Surfactant" *Langmuir*, vol. 10: 3959-3965 (1994).
Howson et al., Design and synthesis of a series of glycerol-derived receptor mediated calcium entry (RMCE) blockers, Eur J Med Chem, vol. 25: 595-602 (1990).

(Continued)

*Primary Examiner* — James C Goloboy
(74) *Attorney, Agent, or Firm* — Nixon & Vanderhye PC

(57) ABSTRACT

To provide a friction-reducing agent containing no sulfur nor phosphorus and being excellent in friction-reducing properties, and a lubricating oil composition using it. An alkanolamine represented by the following formula is used as a friction-reducing agent:

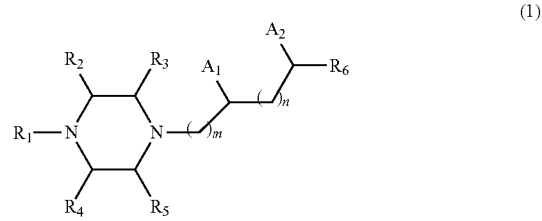

(1)

wherein $A_1$ and $A_2$ are each independently a hydroxy group or a hydrogen atom, provided that $A_1$ and $A_2$ are not hydrogen atoms at the same time, $R_1$ is a hydrocarbon group having at most 30 carbon atoms, $R_2$ to $R_6$ are each independently a hydrogen atom or a hydrocarbon group having at most 30 carbon atoms, and m and n are each independently an integer of from 0 to 10.

2 Claims, No Drawings

(56) References Cited

U.S. PATENT DOCUMENTS

| | | | | |
|---|---|---|---|---|
| 4,248,720 | A | * | 2/1981 | Coupland ............. C07F 11/005 508/378 |
| 4,258,061 | A | * | 3/1981 | Cronin .................... C07C 41/22 514/667 |
| 4,491,583 | A | | 1/1985 | Cronin et al. |
| 4,590,223 | A | * | 5/1986 | Arai .................. C08G 18/2027 502/167 |
| 4,734,350 | A | | 3/1988 | Lin et al. |
| 4,755,601 | A | | 7/1988 | Tahara et al. |
| 4,857,529 | A | | 8/1989 | Tahara et al. |
| 4,885,300 | A | * | 12/1989 | Press ........................ A61P 9/06 514/217.06 |
| 2010/0016186 | A1 | | 1/2010 | Smith |
| 2011/0117125 | A1 | * | 5/2011 | Hope ................. A61K 31/7088 424/204.1 |
| 2012/0225434 | A1 | | 9/2012 | Ciufolini et al. |
| 2014/0295449 | A1 | | 10/2014 | Ciufolini et al. |
| 2016/0274089 | A1 | | 9/2016 | Ciufolini et al. |

FOREIGN PATENT DOCUMENTS

| | | |
|---|---|---|
| JP | 61-285292 | 12/1986 |
| JP | 63-2904 | 1/1988 |
| JP | 7-53983 | 2/1995 |
| JP | 2001-40383 | 2/2001 |
| JP | 2008-37860 | 2/2008 |
| JP | 2011-509258 | 3/2011 |
| JP | 2013-23489 | 2/2013 |
| JP | 2017-159288 | 9/2017 |
| WO | WO 2011/014027 | 2/2011 |

OTHER PUBLICATIONS

Tricerri et al., "Non-anticholinergic gastric acid secretion inhibitors. New piperazine and related derivatives" *Eur. J. Med. Chem. Chimica Therapeutica*, vol. 9, No. 5: 555-562 (1974).

Search Report issued in EP Appln. No. 18744436.9 dated Jun. 30, 2020.

Hromatka et al., "Über unsymmetrisch substituierte Pierazine" *Monatshefte Für Chemie*, vol. 87, No. 6: 701-707 (1956).

Ismaiel et al., "Synthesis of piperazino and morpholino derivatives of aryloxypropane with potential analgesic and possible antimigraine activities" *Medicinal Chemistry Research*, vol. 20, No. 3: 381-387 (2011).

Kafka et al., "Hydroboration of 1,4-Diallylpiperazine" *Collection Czechoslovak Chem. Commun.*, vol. 50, No. 10: 2275-2283 (1985).

Olmo et al., "Diamine and aminoalcohol derivates active against *Trypanosoma brucei*" *Bioorganic & Medicinal Chemistry Letters*, vol. 22, No. 1: 440-443 (2012).

Vignaroli et al., "Prodrugs of Pyrazolo[3,4-d]pyrimidines: From Library Synthesis to Evaluation as Potential Anticancer Agents in an Orthotopic Glioblastoma Model" *Journal of Medicinal Chemistry*, vol. 60, No. 14: 6305-6320 (2017).

Yamawaki et al., "Piperazinealkanol Ester Derivatives of Indomethacin as Dual Inhibitors of 5-Lipoxygenase and Cyclooxygenase" *Chemical and Pharmaceutical Bulletin*, vol. 42, No. 4: 963-971 (1994).

* cited by examiner

ALKANOLAMINE, FRICTION-REDUCING AGENT, AND LUBRICATING OIL COMPOSITION

This application is the U.S. national phase of International Application No. PCT/JP2018/001322 filed 18 Jan. 2018, which designated the U.S. and claims priority to JP Patent Application No. 2017-012379 filed 26 Jan. 2017, and JP Patent Application No. 2017-115863 filed 13 Jun. 2017, the entire contents of each of which are hereby incorporated by reference.

TECHNICAL FIELD

The present invention relates to an alkanolamine, a friction-reducing agent and a lubricating oil composition.

BACKGROUND ART

In recent years, reduction of carbon dioxide gas which has an impact on global warming among environmental problems has been strongly desired. An automobile field is responsible for about one-fifth of carbon dioxide gas emission sources, and trials regarding the improvement of fuel efficiency to reduce carbon dioxide gas have been actively conducted. The techniques to improve fuel efficiency in the automobile field are to reduce engine loss, auxiliary loss, drive train loss and running resistance comprising rolling resistance, air resistance and inertial resistance, and improvement of fuel efficiency is realized by combining various techniques. The engine loss includes friction loss, and reduction of engine or drive train loss includes reduction of friction loss e.g. by an engine oil, in addition to mechanical factors.

Reduction of friction loss by an engine oil is chiefly achieved by reducing flow resistance by lowering the viscosity of the oil. However, simply by lowering the viscosity, the oil film becomes thin, and even at a speed at which an oil having a usual viscosity is in a hydrodynamic lubrication region, a low viscosity oil is in a boundary lubrication region, friction may rather increase and friction loss may occur, or machines may be damaged by abrasion. Accordingly, for the purpose of reducing such friction and abrasion, various additives are blended in a fuel-efficient engine oil.

A friction-reducing agent to be added to a fuel-efficient engine oil is adsorbed on a metal surface to form a coating film, thereby to prevent direct contact of metal members to reduce friction. As typical friction-reducing agents, for example, a suspension of a molybdenum compound and an alkali sulfide, molybdenum oxysulfide dithiocarbamate obtained by reacting carbon disulfide, a secondary amine and a mineral acid (for example, Patent Document 1), molybdenum oxysulfide dithiophosphate (for example, Patent Document 2), a phosphorus molybdenum compound obtained by reducing a hexavalent molybdenum compound with a reducing agent, neutralizing it with a mineral acid containing no phosphorus atom and then reacting it with an acidic phosphoric acid ester (for example, Patent Document 3), an amine salt of molybdic acid obtained by reacting a molybdenum compound and a secondary amine (for example, Patent Document 4), etc. have been proposed.

The friction-reducing agents disclosed in Patent Documents 1 to 3, which contain sulfur or phosphorus, may corrode metals at high temperature or may poison an exhaust gas catalyst.

Further, although the friction-reducing agent disclosed in Patent Document 4 does not contain sulfur or phosphorus, it had problems such that it is inferior in the oil solubility and it is not necessarily sufficient in the friction-reducing properties.

PRIOR ART DOCUMENTS

Patent Documents

Patent Document 1: JP-A-H07-53983
Patent Document 2: JP-A-2001-40383
Patent Document 3: JP-A-2008-37860
Patent Document 4: JP-A-S61-285292

DISCLOSURE OF INVENTION

Technical Problem

Under these circumstances, it is an object of the present invention to provide a friction-reducing agent containing no sulfur nor phosphorus and being excellent in the friction-reducing properties, and a lubricating oil composition containing it.

Solution to Problem

The present inventors have conducted extensive studies to achieve the above object and as a result, found that a specific alkanolamine has excellent friction-reducing properties due to its structural characteristics, and accomplished the present invention.

That is, the present invention provides the following embodiments.

[1] An alkanolamine represented by the following formula (1):

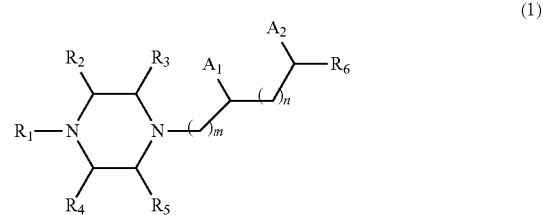

wherein $A_1$ and $A_2$ are each independently a hydroxy group or a hydrogen atom, provided that $A_1$ and $A_2$ are not hydrogen atoms at the same time, $R_1$ is a hydrocarbon group having at most 30 carbon atoms, $R_2$ to $R_6$ are each independently a hydrogen atom or a hydrocarbon group having at most 30 carbon atoms, and m and n are each independently an integer of from 0 to 10.

[2] The alkanolamine according to [1], wherein in the formula (1), $R_1$ is a hydrocarbon group having at least 8 and at most 24 carbon atoms, all of $R_2$ to $R_6$ are hydrogen atoms, m=1 and n=0.

[3] The alkanolamine according to [1] or [2], wherein $A_1$ and $A_2$ are both hydroxy groups.

[4] A method for producing the alkanolamine as defined in [1] or [2], which comprises reacting a raw material amine represented by the following formula (2) with a halide represented by the following formula (3) or an epoxy compound represented by the following formula (4) and further with a halide represented by the following formula (5):

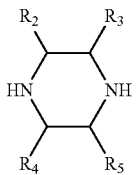
(2)

wherein $R_2$ to $R_5$ are each independently a hydrogen atom or a hydrocarbon group having at most 30 carbon atoms;

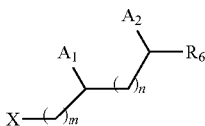
(3)

wherein $A_1$ and $A_2$ are each independently a hydroxy group or a hydrogen atom, provided that $A_1$ and $A_2$ are not hydrogen atoms at the same time, $R_6$ is a hydrogen atom or a hydrocarbon group having at most 30 carbon atoms, X is a halogen atom, and m and n are each independently an integer of from 0 to 10;

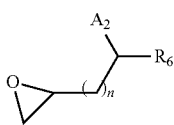
(4)

wherein $A_2$ is a hydroxy group or a hydrogen atom, $R_6$ is a hydrogen atom or a hydrocarbon group having at most 30 carbon atoms, and n is an integer of from 0 to 10;

$R_1$—X (5)

wherein $R_1$ is a hydrocarbon group having at most 30 carbon atoms, and X is a halogen atom.

[5] A method for producing the alkanolamine as defined in [1] or [2], which comprises reacting a raw material amine represented by the following formula (2) with a halide represented by the following formula (5) and further with a halide represented by the following formula (3) or an epoxy compound represented by the following formula (4):

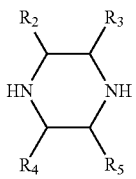
(2)

wherein $R_2$ to $R_5$ are each independently a hydrogen atom or a hydrocarbon group having at most 30 carbon atoms;

$R_1$—X (5)

wherein $R_1$ is a hydrocarbon group having at most 30 carbon atoms, and X is a halogen atom;

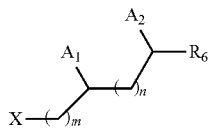
(3)

wherein $A_1$ and $A_2$ are each independently a hydroxy group or a hydrogen atom, provided that $A_1$ and $A_2$ are not hydrogen atoms at the same time, $R_6$ is a hydrogen atom or a hydrocarbon group having at most 30 carbon atoms, X is a halogen atom, and m and n are each independently an integer of from 0 to 10;

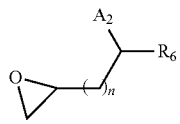
(4)

wherein $A_2$ is a hydroxy group or a hydrogen atom, $R_6$ is a hydrogen atom or a hydrocarbon group having at most 30 carbon atoms, and n is an integer of from 0 to 10.

[6] A friction-reducing agent comprising the alkanolamine as defined in any one of [1] to [3] and a molybdenum compound, in a content of the molybdenum compound of from 0.1 to 3 mol as calculated as molybdenum atoms in the molybdenum compound per 1 mol of the alkanolamine.

[7] The friction-reducing agent according to [6], wherein the molybdenum compound is at least one molybdenum compound selected from the group consisting of molybdenum trioxide, molybdic acid and a molybdate.

[8] The friction-reducing agent according to [6], which further contains a boron compound.

[9] A method for producing the friction-reducing agent as defined in [6] or [7], which comprises mixing an alkanolamine represented by the following formula (1):

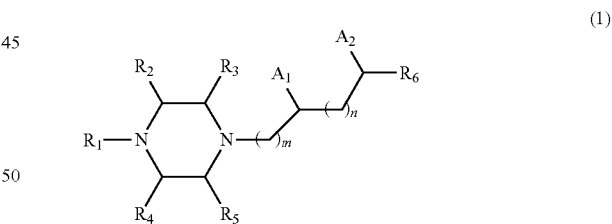
(1)

wherein $A_1$ and $A_2$ are each independently a hydroxy group or a hydrogen atom, provided that $A_1$ and $A_2$ are not hydrogen atoms at the same time, $R_1$ is a hydrocarbon group having at most 30 carbon atoms, $R_2$ to $R_6$ are each independently a hydrogen atom or a hydrocarbon group having at most 30 carbon atoms, and m and n are each independently an integer of from 0 to 10, with a molybdenum compound in a content of the molybdenum compound of from 0.1 to 3 mol as calculated as molybdenum atoms in the molybdenum compound per 1 mol of the alkanolamine, and heating the mixture.

[10] A lubricating oil composition comprising the friction-reducing agent as defined in any one of [6] to [8] and a lubricating oil.

[11] The lubricating oil composition according to [10], which further contains a zinc dithiophosphate-based abrasion inhibitor.

[12] A lubricating oil containing the alkanolamine as defined in [1] or [3].

Advantageous Effects of Invention

According to the present invention, an alkanolamine suitable for a friction-reducing agent, a friction-reducing agent excellent in the friction-reducing properties, and a lubricating oil composition are provided. The alkanolamine and the friction-reducing agent of the present invention are characterized by containing no sulfur nor phosphorus and having low environmental burden.

DESCRIPTION OF EMBODIMENTS

Now, the present invention will be described in further detail.

The alkanolamine of the present invention is characterized by being represented by the formula (1).

In the formula (1), $A_1$ and $A_2$ are each independently a hydroxy group or a hydrogen atom, and $A_1$ and $A_2$ are not hydrogen atoms at the same time. With a view to obtaining favorable friction-reducing properties, $A_1$ and $A_2$ in the formula (1) are particularly preferably both hydroxy groups.

In the formula (1), $R_1$ is a hydrocarbon group having at most 30 carbon atoms, and $R_2$ to $R_6$ are each independently a hydrogen atom or a hydrocarbon group having at most 30 carbon atoms.

The hydrocarbon having at most 30 carbon atoms may, for example, be an alkyl group, an alkenyl group, an aryl group, a cycloalkyl group or a cycloalkenyl group, having at most 30 carbon atoms.

The alkyl group having at most 30 carbon atoms may, for example, be a methyl group, an ethyl group, or a linear or branched propyl group, butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, eicosyl group, heneicosyl group, docosyl group, tricosyl group or tetracosyl group.

The alkenyl group having at most 30 carbon atoms may, for example, be a propenyl group, a butenyl group, a pentenyl group, a hexenyl group, a heptenyl group, an octenyl group, a nonenyl group, a decenyl group, an undecenyl group or a dodecenyl group.

The aryl group having at most 30 carbon atoms may, for example, be a phenyl group, a toluyl group, a xylyl group, a cumenyl group, a mesityl group, a benzyl group, a phenethyl group, a styryl group, a cinnamyl group, a benzhydryl group, a trityl group, an ethylphenyl group, a propylphenyl group, a butylphenyl group, a pentylphenyl group, a hexylphenyl group, a heptylphenyl group, an octylphenyl group, a nonylphenyl group, a decylphenyl group, an undecylphenyl group, a dodecylphenyl group, a styrenated phenyl group, a p-cumylphenyl group, a phenylphenyl group, a benzylphenyl group, an α-naphthyl group or a β-naphthyl group.

The cycloalkyl group and cycloalkenyl group, having at most 30 carbon atoms, may, for example, be a cyclopentyl group, a cyclohexyl group, a cycloheptyl group, a methylcyclopentyl group, a methylcyclohexyl group, a methylcycloheptyl group, a cyclopentenyl group, a cyclohexenyl group, a cycloheptenyl group, a methylcyclopentenyl group, a methylcyclohexenyl group or a methylcycloheptenyl group.

Among these hydrocarbon groups, $R_1$ to $R_6$ are preferably an alkyl group having at most 30 carbon atoms, more preferably a $C_{8-24}$ alkyl group.

It is preferred that all of $R_2$ to $R_6$ are hydrogen atoms, in view of easy preparation of the alkanolamine.

$R_1$ is, in view of excellent oil solubility of the alkanolamine, preferably a $C_{8-24}$ alkyl group, more preferably an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a heneicosyl group, a docosyl group, a tricosyl group or a tetracosyl group.

In the formula (1), m and n represent the number of methylene groups, and are each independently an integer of from 0 to 10. It is preferred that m and n are each independently an integer of from 0 to 3, and in view of excellent friction-reducing properties, it is particularly preferred that m=1 and n=0.

The alkanolamine in the present invention may, for example, be specifically 3-(4-octyl-1-piperazinyl)-1,2-propanediol, 3-(4-(2-ethylhexyl)-1-piperazinyl)-1,2-propanediol, 3-(4-nonyl-1-piperazinyl)-1,2-propanediol, 3-(4-decyl-1-piperazinyl)-1,2-propanediol, 3-(4-undecyl-1-piperazinyl)-1,2-propanediol, 3-(4-dodecyl-1-piperazinyl)-1,2-propanediol, 3-(4-tridecyl-1-piperazinyl)-1,2-propanediol, 3-(4-tetradecyl-1-piperazinyl)-1,2-propanediol, 3-(4-hexadecyl-1-piperazinyl)-1,2-propanediol, 3-(4-heptadecyl-1-piperazinyl)-1,2-propanediol, 3-(4-octadecyl-1-piperazinyl)-1,2-propanediol, 3-(4-nonadecyl-1-piperazinyl)-1,2-propanediol, 3-(4-eicosyldecyl-1-piperazinyl)-1,2-propanediol, 3-(4-heneicosyldecyl-1-piperazinyl)-1,2-propanediol, 3-(4-docosyl-1-piperazinyl)-1,2-propanediol, 3-(4-tricosyl-1-piperazinyl)-1,2-propanediol, 3-(4-tetracosyl-1-piperazinyl)-1,2-propanediol, 3-(4-phenyl-1-piperazinyl)-1,2-propanediol, 3-(4-benzyl-1-piperazinyl)-1,2-propanediol, 3-(4-cyclohexyl-1-piperazinyl)-1,2-propanediol, 4-(4-dodecyl-1-piperazinyl)-1,2-butanediol, 4-(4-dodecyl-1-piperazinyl)-1,3-butanediol, 4-(4-dodecyl-1-piperazinyl)-2,3-butanediol, 5-(4-dodecyl-1-piperazinyl)-1,2-pentanediol, 6-(4-dodecyl-1-piperazinyl)-1,2-hexanediol, 8-(4-dodecyl-1-piperazinyl)-1,2-octanediol, 4-dodecyl-1-piperazineethanol, 4-dodecyl-1-piperazinepropanol, 3-(4-(2-octyldodecyl)-1-piperazinyl)-1,2-propanediol, 3-(4-(2-hexyldecyl)-1-piperazinyl)-1,2-propanediol, 3-(4-(2-decyltetradecyl)-1-piperazinyl)-1,2-propanediol, 3-(4-isostearyl-1-piperazinyl)-1,2-propanediol or 3-(4-oleyl-1-piperazinyl)-1,2-propanediol.

The alkanolamine of the present invention may be produced by reacting a raw material alkanolamine with a halide or an epoxy compound. Further, the raw material alkanolamine may be produced by reacting a raw material amine with a halide containing a hydroxy group or an epoxy compound.

In the above reaction, the reaction temperature is not particularly limited, however, with a view to obtaining a desired product with a favorable yield, it is preferably from 40° C. to 200° C., particularly preferably from 60° C. to 150° C.

For the reaction, a solvent may be used. The solvent is not particularly limited and may, for example, be a hydrocarbon organic solvent such as hexane, cyclohexane, octane, isooctane, benzene, toluene, xylene or paraffin, an alcohol organic solvent such as methanol, ethanol, isopropanol, butanol, ethylene glycol or propylene glycol, or an aprotic polar solvent such as diethyl ether, dibutyl ether, ethylene glycol dimethyl ether, diethylene glycol dimethyl ether, tetrahydrofuran, dimethylformamide or dimethylsufoxide. They may be used alone or as a mixture of two or more.

For the reaction, a catalyst may be used. The catalyst is not particularly limited and may, for example, be an alkali metal carbonate such as potassium carbonate, sodium carbonate, lithium carbonate or cesium carbonate, an alkaline earth metal carbonate such as magnesium carbonate or calcium carbonate, an alkali metal hydrogen carbonate such as sodium hydrogen carbonate or potassium hydrogen carbonate, an alkali metal hydroxide such as sodium hydroxide, potassium hydroxide or lithium hydroxide, an alkaline earth metal hydroxide such as magnesium hydroxide or calcium hydroxide, or a basic substance such as sodium methoxide or sodium ethoxide.

The raw material amine used for production of the alkanolamine of the present invention is not particularly limited and may, for example, be piperazine or a piperazine derivative. Specifically, although it is not particularly limited, it may, for example, be piperazine, 2-methyl-piperazine, 1-octyl-piperazine, 1-(2-ethylhexyl)-piperazine, 1-nonyl-piperazine, 1-decyl-piperazine, 1-undecyl-piperazine, 1-dodecyl-piperazine, 1-tridecyl-piperazine, 1-tetradecyl-piperazine, 1-tetradecyl-piperazine, 1-hexadecyl-piperazine, 1-heptadecyl-piperazine, 1-octadecyl-piperazine, 1-nonadecyl-piperazine, 1-eicosyldecyl-piperazine, 1-heneicosyldecyl-piperazine, 1-docosyl-piperazine, 1-tricosyl-piperazine, 1-tetracosyl-piperazine, 1-phenyl-piperazine, 1-benzyl-piperazine or 1-cyclohexyl-piperazine.

The raw material alkanolamine used for production of the alkanolamine of the present invention is not particularly limited and may, for example, be 3-(1-piperazinyl)-1, 2-propanediol, 4-(1-piperazinyl)-1, 3-butanediol, 4-(1-piperazinyl)-2, 3-butanediol, 5-(1-piperazinyl)-1, 2-pentanediol, 6-(1-piperazinyl)-1, 2-hexanediol, 8-(1-piperazinyl)-1, 2-octanediol, 1-piperazinemethanol, 1-piperazineethanol, 1-piperazinepropanol, 1-piperazinebutanol, 1-piperazinepentanol, 1-piperazinehexanol, 1-piperazineheptanol or 1-piperazineoctanol.

The halide used for production of the alkanolamine of the present invention is not particularly limited and may, for example, be a brominated hydrocarbon, chlorinated hydrocarbon, iodinated hydrocarbon or fluorinated hydrocarbon, having at most 30 carbon atoms, and they may have one or two hydroxy groups in its molecule.

The epoxy compound used for production of the alkanolamine of the present invention is not particularly limited and may be an epoxy hydrocarbon group having at most 10 carbon atoms, and may have one hydroxy group in its molecule. It may, for example, be specifically, glycidol, ethylene oxide or propylene oxide.

After completion of the reaction, the alkanolamine of the present invention can be obtained by means of a conventional purification method such as extraction, filtration, crystallization, distillation or chromatography by itself or suitably in combination.

A specific method for producing the alkanolamine of the present invention is not particularly limited and may, for example, be a method of reacting a raw material amine represented by the following formula (2) with a halide represented by the following formula (3) or an epoxy compound represented by the following formula (4) and further with a halide represented by the following formula (5) or a method of reacting a raw material amine represented by the following formula (2) with a halide represented by the following formula (5) and further with a halide represented by the following formula (3) or an epoxy compound represented by the following formula (4).

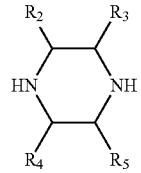
(2)

wherein $R_2$ to $R_5$ are each independently a hydrogen atom or a hydrocarbon group having at most 30 carbon atoms;

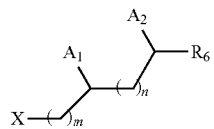
(3)

wherein $A_1$ and $A_2$ are each independently a hydroxy group or a hydrogen atom, provided that $A_1$ and $A_2$ are not hydrogen atoms at the same time, $R_6$ is a hydrogen atom or a hydrocarbon group having at most 30 carbon atoms, X is a halogen atom, and m and n are each independently an integer of from 0 to 10;

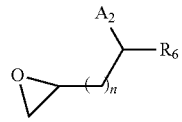
(4)

wherein $A_2$ is a hydroxy group or a hydrogen atom, $R_6$ is a hydrogen atom or a hydrocarbon group having at most 30 carbon atoms, and n is an integer of from 0 to 10;

$$R_1—X \qquad (5)$$

wherein $R_1$ is a hydrocarbon group having at most 30 carbon atoms, and X is a halogen atom.

In the formulae (3) and (5), X is a halogen atom, and the halogen atom is not particularly limited and may, for example, be a bromine atom, a chlorine atom, an iodine atom or a fluorine atom.

The alkanolamine compound of the present invention may be used as a composition or an additive of a lubricating oil. A composition containing the alkanolamine of the present invention and a molybdenum compound may be used as a friction-reducing agent for a lubricating oil, although it is not particularly limited.

The friction-reducing agent of present invention is preferably a composition containing the above alkanolamine and a molybdenum compound, and the composition preferably contains the molybdenum compound in a content of from 0.1 to 3 mol as calculated as molybdenum atoms in the molybdenum compound per 1 mol of the alkanolamine. The molybdenum content is, in view of excellent friction-reducing properties, preferably from 0.5 to 1.5 mol. If the amount of the molybdenum atoms is less than 0.1 mol, no satisfactory friction-reducing properties will be obtained, and if it exceeds 3 mol, the oil solubility may decrease.

The molybdenum compound in the friction-reducing agent of the present invention is a compound having molybdenum in its molecule and is not particularly limited. It may, for example, be molybdenum trioxide, molybdic acid, an alkali metal molybdate or ammonium molybdate. They may be used alone or as a mixture of two or more. Considering the oil solubility and friction properties, among them, molybdenum trioxide is particularly preferred.

The method for producing the friction-reducing agent of the present invention is not particularly limited and may, for example, be a method of mixing the alkanolamine of the present invention and the molybdenum compound in a content of the molybdenum compound of from 0.1 to 3 mol as calculated as molybdenum atoms in the molybdenum compound per 1 mol of the alkanolamine, and heating the mixture. The temperature at the time of heating is not particularly limited, and is preferably from 40° C. to 200° C., particularly preferably from 60° C. to 120° C., whereby a composition having favorable oil solubility is obtained. In the method, a solvent may be used, and a solvent which can be used is not particularly limited and may, for example, be a hydrocarbon organic solvent such as hexane, cyclohexane, octane, isooctane, benzene, toluene, xylene or paraffin, an alcohol organic solvent such as methanol, ethanol, isopropanol, butanol, ethylene glycol or propylene glycol, an aprotic polar solvent such as diethylene ether, dibutyl ether, ethylene glycol dimethyl ether, diethylene glycol dimethyl ether, tetrahydrofuran, dimethylformamide or dimethylsulfoxide, a fuel oil such as gasoline, gas oil, kerosene, mineral oil or polybutene, a lubricating oil such as a mineral oil, a synthetic oil, a vegetable oil or an animal oil (including an unmixed lubricating oil, and a lubricating oil containing additives such as a detergent dispersant, an antioxidant, a load carrying additive, a rust inhibitor, a corrosion inhibitor, a viscosity index improver, a pour point depressant, an anti-foam additive, an emulsifying agent, an anti-emulsifying agent, and a microbiocide), or water. They may be used alone or as a mixture of two or more.

In production of the friction-reducing agent of the present invention, after mixing and heating, as the case requires, the solvent may be removed e.g. by vacuum distillation, or the mixture may be used as it is without removing the solvent.

The lubricating oil composition of the present invention is characterized by containing the friction-reducing agent of the present invention and the lubricating oil (including an unmixed lubricating oil and a lubricating oil containing additives). The lubricating oil is not particularly limited and may, for example, be an automobile lubricating oil such as a gasoline engine oil, a Diesel engine oil or a vehicle gear oil, a ship lubricating oil such as a ship engine oil, or an industrial lubricating oil such as a machine oil, a metal processing oil or an electrical insulating oil.

The lubricating oil composition of the present invention may contain an abrasion inhibitor other than the friction-reducing agent of the present invention, within a range not to impair the effects of the present invention, whereby the lubricating oil composition will have more favorable friction-reducing properties. Such an abrasion inhibitor is preferably a zinc dithiophosphate abrasion inhibitor, and may, for example, be zinc dialkyldithiophosphate, zinc diaryldithiophosphate or zinc alkylaryldithiophosphate. As commercial products, specifically, Lz 677A, Lz 1095, Lz 1097, Lz 1370, Lz 1371, Lz 1373 and Lz 1395 commercially available from The Lubrizol Corporation, OLOA 260, OLOA 262, OLOA 267 and OLOA 269R commercially available from Chevron Oronite, HITEC 7169 and HITEC 7197 commercially available from Afton Chemical Corporation, and ADEKA KIKU-LUBE Z-112 available from ADEKA CORPORATION.

The friction-reducing agent of the present invention may further contain a boron compound, whereby more favorable friction-reducing properties at low temperature will be obtained. The boron compound used is not particularly limited and may, for example, be an aminoborane compound such as tris(dimethylamino)borane or tris(diethylamino)borane, a borate ester such as trimethyl borate, triethyl borate, tripropyl borate, tributyl borate, tripentyl borate, trihexyl borate, trioctyl borate, tridecyl borate, tritetradecyl borate, triphenyl borate, triethanolamine borate, triisopropanolamine borate, 2-ethoxy-4,4,5,5-tetramethyl-1,3,2-dioxoborolane, 2-isopropoxy-4,4,5,5-tetramethyl-1,3,2-dioxoborolane, 2-isopropoxy-4,4,6-trimethyl-1,3,2-dioxaborinane, 2-methoxy-4,4,5,5-tetramethyl-1,3,2-dioxoborolane, 2,4,6-trimethylboroxine, tris(trimethylsilyl)borate or tris(2-cyanoethyl)borate, a boronic acid compound such as ethyl boronate, propyl boronate, butyl boronate, pentyl boronate, hexyl boronate, octyl boronate, decyl boronate, dodecyl boronate, tridecyl boronate, tetradecyl boronate, cyclohexyl boronate, cyclopentyl boronate or 1-cyclopentenyl boronate, or a boron dispersed alkenyl succinimide. The amount of the boron compound blended (that is, the content in the friction-reducing agent) is preferably within a range of from 0.01 to 3.0 wt %, particularly preferably within a range of from 0.05 to 2.0 wt %, in view of excellent balance between the friction-reducing properties particularly at low temperature and oil solubility.

EXAMPLES

Now, the present invention will be described in further detail with reference to Examples. However, it should be understood that the present invention is by no means restricted to such specific Examples. Reagents etc. used were commercial products unless otherwise specified.

Analytical instruments and evaluation methods employed in Examples are described below.

<NMR Measurement>

NMR measuring apparatus: VARIAN Gemini-200.

<Elemental Analysis>

Elemental analyzer: automatic elemental analysis apparatus 240011, manufactured by Perkin Elmer Japan Co., Ltd.

Oxygen flask combustion IC measurement method: Ion Chromatograph IC-2001 manufactured by TOSOH CORPORATION.

<Evaluation of Oil Solubility>

The obtained amine molybdate composition was mixed with toluene so that the concentration of the amine molybdate concentration would be 1 wt %, followed by stirring with heating at 80° C. for dissolution. The state of the solution after left to stand overnight was visually observed and taken as the index of the oil solubility.

(Evaluation standard)

A: A solution state without precipitates or suspension.

B: A suspension state.

C: A state with separation or precipitates observed.

<Evaluation of Friction Properties>

The obtained friction-reducing agent was blended with base oil (C-1, manufactured by Exxon Mobil Corporation, SpectraSyn Plus 6) so that the molybdenum concentration would be 500 ppm. Further, zinc dialkyldithiophosphate (ZnDTP, manufactured by ADEKA CORPORATION, KIKU-LUBE Z-112) as an abrasion inhibitor was blended so that the zinc concentration would be 1,000 ppm.

Of a blended oil prepared in the after-described Examples, the coefficient of friction was evaluated by using Friction Player (manufactured by RHESCA CO., LTD., FPR2100) by ball-on-disk method at 120° C. at a rotational speed of 477.5 rpm under a load of 10 N. For the ball and the disk, lapped SUJ2 was used. The average of coefficients of friction measured for one hour was calculated.
(Evaluation Standards)
A: Coefficient of friction being less than 0.075.
B: Coefficient of friction being at least 0.075 and less than 0.10.
C: Coefficient of friction being at least 0.10.

<Evaluation of Low Temperature Friction Properties>

Of a blended oil prepared in the after-described Examples, the coefficient of friction was evaluated by using Friction Player (manufactured by RHESCA CO., LTD., FPR2100) by ball-on-disk method at 80° C. at a rotational speed of 477.5 rpm under a load of 10 N. For the ball and the disk, lapped SUJ2 was used. The average of coefficients of friction measured for 3 hours was calculated.
(Evaluation Standards)
A: Coefficient of friction being less than 0.075.
B: Coefficient of friction being at least 0.075 and less than 0.10.
C: Coefficient of friction being at least 0.10.

Example 1

Into a 1 L four-necked flask equipped with a stirring machine and a condenser tube, 74.4 g (0.47 mol) of 3-(1-piperazinyl)-1,2-propanediol, 38.6 g (0.16 mol) of dodecyl bromide, isopropanol (500 g) and 17.3 g (0.16 mol) of sodium carbonate were added, followed by heating at 90° C. for 8 hours in a stream of nitrogen. After completion of heating, sodium carbonate was removed by filtration, and 2-propanol was removed by vacuum distillation. Then, only the oil layer was collected by extraction with chloroform, which was subjected to vacuum distillation and vacuum drying to obtain 48.58 g (yield: 95.4%) of white crystalline 3-(4-dodecyl-1-piperazinyl)-1,2-propanediol. Identification was conducted from the results of $^1$H-NMR measurement, $^{13}$C-NMR measurement and elemental analysis.

$^1$H-NMR (CDCl$_3$): 3.72-3.84 (m, 2H), 3.48-3.53 (dd, 1H), 2.29-2.70 (m, 12H), 1.47 (s, 2H), 1.19-1.26 (m, 18H), 0.86-0.90 (t, 3H) [ppm]

$^{13}$C-NMR (CDCl$_3$): 66.85, 65.00, 60.44, 58.73, 53.35, 53.23, 31.86, 29.61, 29.58, 29.56, 29.53, 29.29, 27.56, 26.81, 22.63, 14.05 [ppm]

Elemental analysis (calculated value): C=69.5, H=12.3, N=8.5,

Elemental analysis (measured value): C=69.6, H=12.8, N=8.5.

Then, into a 100 mL round bottom flask, 3.29 g of 3-(4-dodecyl-1-piperazinyl)-1,2-propanediol and 10 g of toluene were added, followed by heating at 80° C. for dissolution, and an aqueous molybdenum dispersion having 1.51 g of molybdenum trioxide dispersed in 10 g of water was dropwise added. On that occasion, the Mo atom/amine (molar ratio) was 1.05. Then, the reaction mixture was aged at 80° C. for 2 hours and at 110° C. for 1 hour. After completion, unreacted molybdenum trioxide was removed by filtration, and the solvent was removed by vacuum distillation and vacuum drying to obtain 3.58 g of liver brown solid friction-reducing agent (A-1). The molybdenum content in the friction-reducing agent (A-1) was 13.2 wt %.

Using the obtained friction-reducing agent (A-1), oil solubility and friction properties were evaluated, and the results are shown in Table 1. The friction-reducing agent (A-1) was excellent in oil solubility, had a low coefficient of friction and had favorable friction-reducing properties.

TABLE 1

|  |  | Example 1 | Example 2 |
|---|---|---|---|
| Friction-reducing agent |  | A-1 | A-2 |
| Amine | Name | 3-(4-dodecyl-1-piperazinyl)-1,2-propanediol | 3-(4-hexadecyl-1-piperazinyl)-1,2-propanediol |
|  | Structural formula | $C_{12}H_{25}$—N(piperazine)N—CH$_2$CH(OH)CH$_2$OH | $C_{16}H_{33}$—N(piperazine)N—CH$_2$CH(OH)CH$_2$OH |
| Molybdenum |  | MoO$_3$ | MoO$_3$ |
| Mo/amine (molar ratio) |  | 1.05 | 0.5 |
| Mo content (wt %) |  | 13.2 | 9.3 |
| Oil solubility | Results | Soluble | Soluble |
|  | Evaluation | A | A |
| Friction properties | Coefficient of friction | 0.052 | 0.044 |
|  | Evaluation | A | A |

|  |  | Example 3 | Example 4 |
|---|---|---|---|
| Friction-reducing agent |  | A-3 | A-4 |
| Amine | Name | 3-(4-octadecyl-1-piperazinyl)-1,2-propanediol | 3-(4-dodecyl-1-piperazinyl)-1,2-propanediol |

TABLE 1-continued

| | | | |
|---|---|---|---|
| Structural formula | $C_{18}H_{37}-N\underset{}{\diagdown}N-\text{CH}_2\text{CH(OH)CH}_2\text{OH}$ (piperazine ring) | | $C_{12}H_{25}-N\underset{}{\diagdown}N-\text{CH}_2\text{CH(OH)CH}_2\text{OH}$ |
| Molybdenum | | $MoO_3$ | $MoO_3$ |
| Mo/amine (molar ratio) | | 1.05 | 1.5 |
| Mo content (wt %) | | 8.2 | 21.7 |
| Oil solubility | Results | Soluble | Soluble |
| | Evaluation | A | A |
| Friction properties | Coefficient of friction | 0.072 | 0.069 |
| | Evaluation | A | A |

TABLE 2

| | | Example 5 | Example 6 |
|---|---|---|---|
| Friction-reducing agent | | A-5 | A-6 |
| Amine | Name | 3-(4-(2-ethylhexyl)-1-piperazinyl)-1,2-propanediol | 4-dodecyl-1-piperazineethanol |
| | Structural formula | (2-ethylhexyl)-piperazine-CH$_2$CH(OH)CH$_2$OH | $C_{12}H_{25}$-piperazine-CH$_2$CH$_2$OH |
| Molybdenum | | $MoO_3$ | $MoO_3$ |
| Mo/amine (molar ratio) | | 1.05 | 1.05 |
| Mo content (wt %) | | 16.3 | 6.4 |
| Oil solubility | Results | Soluble | Soluble |
| | Evaluation | A | A |
| Friction properties | Coefficient of friction | 0.089 | 0.066 |
| | Evaluation | B | A |

| | | Example 7 | Example 8 |
|---|---|---|---|
| Friction-reducing agent | | A-7 | A-8 |
| Amine | Name | 3-(4-(2-decyltetradecyl)-1-piperazinyl)-1,2-propanediol | 3-(4-(2-decyltetradecyl)-1-piperazinyl)-1,2-propanediol |
| | Structural formula | $C_{10}H_{21}$, $C_{12}H_{25}$-branched piperazine-CH$_2$CH(OH)CH$_2$OH | $C_{10}H_{23}$, $C_{12}H_{25}$-branched piperazine-CH$_2$CH(OH)CH$_2$OH |
| Molybdenum | | $MoO_3$ | $MoO_3$ |
| Mo/amine (molar ratio) | | 1.05 | 0.75 |
| Mo content (wt %) | | 12.7 | 8.8 |
| Oil solubility | Results | Soluble | Soluble |
| | Evaluation | A | A |
| Friction properties | Coefficient of friction | 0.045 | 0.51 |
| | Evaluation | A | A |

Example 2

Into a 1 L four-necked flask equipped with a stirring machine and a condenser tube, 74.4 g (0.47 mol) of 3-(1-piperazinyl)-1,2-propanediol, 47.3 g (0.16 mol) of hexadecyl bromide, isopropanol (500 g) and 17.3 g (0.16 mol) of sodium carbonate were added, followed by heating at 90° C. for 8 hours in a stream of nitrogen. After completion of heating, sodium carbonate was removed by filtration, and 2-propanol was removed by vacuum distillation. Then, only the oil layer was collected by extraction with chloroform, which was subjected to vacuum distillation and vacuum drying to obtain 56.6 g (yield: 94.9%) of white crystalline 3-(4-hexadecyl-1-piperazinyl)-1,2-propanediol.

Identification was conducted from the results of $^1$H-NMR measurement, $^{13}$C-NMR measurement and elemental analysis.

$^1$H-NMR (CDCl$_3$): 3.72-3.86 (m, 2H), 3.43-3.54 (dd, 1H), 2.34-2.75 (m, 12H), 1.50 (s, 2H), 1.19-1.26 (m, 26H), 0.86-0.90 (t, 3H) [ppm].

$^{13}$C-NMR (CDCl$_3$): 67.25, 65.26, 60.76, 58.89, 53.28, 32.16, 29.93, 29.90, 29.85, 29.82, 29.79, 29.60, 27.78, 26.88, 22.92, 14.36 [ppm].

Elemental analysis (calculated value): C=71.8, H=12.6, N=7.3,

Elemental analysis (measured value): C=71.8, H=12.8, N=7.3.

Then, into a 100 mL round bottom flask, 3.85 g of 3-(4-hexadecyl-1-piperazinyl)-1,2-propanediol and 10 g of toluene were added, followed by heating at 80° C. for dissolution, and an aqueous molybdenum dispersion having 0.72 g of molybdenum trioxide dispersed in 10 g of water was dropwise added. On that occasion, the Mo atom/amine (molar ratio) was 0.5. Then, the reaction mixture was aged at 80° C. for 2 hours and at 110° C. for 1 hour. After completion, unreacted molybdenum trioxide was removed by filtration, and the solvent was removed by vacuum distillation and vacuum drying to obtain 4.35 g of deep green solid friction-reducing agent (A-2). The molybdenum content in the friction-reducing agent (A-2) was 9.2 wt %.

Using the obtained friction-reducing agent (A-2), oil solubility and friction properties were evaluated, and the results are shown in Table 1. The friction-reducing agent (A-2) was excellent in oil solubility, had a low coefficient of friction and had favorable friction-reducing properties.

Example 3

Into a 1 L four-necked flask equipped with a stirring machine and a condenser tube, 38.4 g (0.24 mol) of 3-(1-piperazinyl)-1,2-propanediol, 25.8 g (0.08 mol) of octadecyl bromide, isopropanol (250 g) and 8.65 g (0.08 mol) of sodium carbonate were added, followed by heating at 90° C. for 8 hours in a stream of nitrogen. After completion of heating, sodium carbonate was removed by filtration, and 2-propanol was removed by vacuum distillation. Then, only the oil layer was collected by extraction with chloroform, which was subjected to vacuum distillation and vacuum drying to obtain 30.8 g (yield: 95.9%) of white crystalline 3-(4-octadecyl-1-piperazinyl)-1,2-propanediol.

Identification was conducted from the results of $^1$H-NMR measurement, $^{13}$C-NMR measurement and elemental analysis.

$^1$H-NMR (CDCl$_3$): 3.71-3.90 (m, 2H), 3.49-3.55 (dd, 1H), 2.43-2.84 (m, 12H), 1.55 (s, 2H), 1.19-1.25 (m, 30H), 0.86-0.90 (t, 3H) [ppm].

$^{13}$C-NMR (CDCl$_3$): 67.36, 65.07, 60.54, 58.67, 52.96, 32.17, 29.95, 29.91, 29.85, 29.82, 29.74, 29.61, 27.68, 26.53, 22.94, 14.37 [ppm].

Elemental analysis (calculated value): C=72.8, H=12.7, N=6.8,

Elemental analysis (calculated value): C=73.0, H=13.0, N=6.8.

Then, into a 100 mL round bottom flask, 4.13 g of 3-(4-octadecyl-1-piperazinyl)-1,2-propanediol and 10 g of toluene were added, followed by heating at 80° C. for dissolution, and an aqueous molybdenum dispersion having 1.51 g of molybdenum trioxide dispersed in 10 g of water was dropwise added. On that occasion, the Mo atom/amine (molar ratio) was 1.05. Then, the reaction mixture was aged at 80° C. for 2 hours and at 110° C. for 1 hour. After completion, unreacted molybdenum trioxide was removed by filtration, and the solvent was removed by vacuum distillation and vacuum drying to obtain 4.74 g of deep green solid friction-reducing agent (A-3). The molybdenum content in the friction-reducing agent (A-3) was 8.2 wt %.

Using the obtained friction-reducing agent (A-3), oil solubility and friction properties were evaluated, and the results are shown in Table 1. The friction-reducing agent (A-3) was excellent in oil solubility, had a low coefficient of friction and had favorable friction-reducing properties.

Example 4

Into a 100 mL round bottom flask, 3.29 g of 3-(4-dodecyl-1-piperazinyl)-1,2-propanediol prepared in Example 1 and 10 g of toluene were added, followed by heating at 80° C. for dissolution, and an aqueous molybdenum dispersion having 2.15 g of molybdenum trioxide dispersed in 10 g of water was dropwise added. On that occasion, the Mo atom/amine (molar ratio) was 1.5. Then, the reaction mixture was aged at 80° C. for 2 hours and at 110° C. for 1 hour. After completion, unreacted molybdenum trioxide was removed by filtration, and the solvent was removed by vacuum distillation and vacuum drying to obtain 4.12 g of liver brown solid friction-reducing agent (A-4). The molybdenum content in the friction-reducing agent (A-4) was 21.7 wt %.

Using the obtained friction-reducing agent (A-4), oil solubility and friction properties were evaluated, and the results are shown in Table 1. The friction-reducing agent (A-4) was excellent in oil solubility, had a low coefficient of friction and had favorable friction-reducing properties.

Example 5

Into a 1 L four-necked flask equipped with a stirring machine and a condenser tube, 38.4 g (0.24 mol) of 3-(1-piperazinyl)-1,2-propanediol, 15.4 g (0.08 mol) of 2-ethylhexyl bromide, isopropanol (250 g) and 8.65 g (0.08 mol) of sodium carbonate were added, followed by heating at 90° C. for 8 hours in a stream of nitrogen. After completion of heating, sodium carbonate was removed by filtration, and 2-propanol was removed by vacuum distillation. Then, only the oil layer was collected by extraction with chloroform, which was subjected to vacuum distillation and vacuum drying to obtain 20.1 g (yield: 92.2%) of white crystalline 3-(4-(2-ethylhexyl)-1-piperazinyl)-1,2-propanediol.

Identification was conducted from the results of $^1$H-NMR measurement, $^{13}$C-NMR measurement and elemental analysis.

$^1$H-NMR (CDCl$_3$): 3.69-3.86 (m, 2H), 3.49-3.55 (dd, 1H), 2.14-2.70 (m, 12H), 1.26-1.46 (m, 9H), 0.82-0.89 (m, 6H) [ppm].

$^{13}$C-NMR (CDCl$_3$): 67.18, 65.32, 63.07, 60.78, 53.66, 36.30, 31.62, 29.13, 24.81, 23.35, 14.38, 10.95 [ppm].

Elemental analysis (calculated value): C=66.1, H=11.8, N=10.3,

Elemental analysis (measured value): C=66.2, H=12.0, N=10.4.

Then, into a 100 mL round bottom flask, 3.54 g of 3-(4-(2-ethylhexyl)-1-piperazinyl)-1,2-propanediol and 10 g of toluene were added, followed by heating at 80° C. for dissolution, and an aqueous molybdenum dispersion having 1.97 g of molybdenum trioxide dispersed in 10 g of water was dropwise added. On that occasion, the Mo atom/amine (molar ratio) was 1.05. Then, the reaction mixture was aged at 80° C. for 2 hours and at 110° C. for 1 hour. After completion, unreacted molybdenum trioxide was removed by filtration, and the solvent was removed by vacuum distillation and vacuum drying to obtain 3.39 g of deep green solid friction-reducing agent (A-5). The molybdenum content in the friction-reducing agent (A-5) was 16.3 wt %.

Using the obtained friction-reducing agent (A-5), oil solubility and friction properties were evaluated, and the results are shown in Table 2. The friction-reducing agent (A-5) was excellent in oil solubility, had a low coefficient of friction and had favorable friction-reducing properties.

Example 6

Into a 1 L four-necked flask equipped with a stirring machine and a condenser tube, 31.2 g (0.24 mol) of 1-piperazineethanol, 19.3 g (0.08 mol) of dodecyl bromide, isopropanol (250 g) and 8.65 g (0.08 mol) of sodium carbonate were added, followed by heating at 90° C. for 8 hours in a stream of nitrogen. After completion of heating, sodium carbonate was removed by filtration, and 2-propanol was removed by vacuum distillation. Then, only the oil layer was collected by extraction with chloroform, which was subjected to vacuum distillation and vacuum drying to obtain 23.55 g (yield: 94.2%) of white crystalline 4-dodecyl-1-piperazineethanol.

Identification was conducted from the results of $^1$H-NMR measurement, $^{13}$C-NMR measurement and elemental analysis.

$^1$H-NMR (CDCl$_3$): 3.67-3.70 (t, 2H), 2.80 (m, 8H), 2.65-2.68 (t, 2H), 2.51-2.56 (t, 2H), 1.61 (s, 2H), 1.19-1.26 (m, 18H), 0.86-0.90 (t, 3H) [ppm].

$^{13}$C-NMR (CDCl$_3$): 59.52, 58.43, 57.88, 52.54, 52.12, 32.09, 29.81, 29.75, 29.60, 29.56, 29.52, 27.52, 26.08, 22.86, 14.32 [ppm].

Elemental analysis (calculated value): C=72.4, H=12.8, N=9.4,

Elemental analysis (measured value): C=72.4, H=12.9, N=9.4.

Then, into a 100 mL round bottom flask, 4.48 g of 4-dodecyl-1-piperazineethanol and 15 g of toluene were added, followed by heating at 80° C. for dissolution, and an aqueous molybdenum dispersion having 2.16 g of molybdenum trioxide dispersed in 15 g of water was dropwise added. On that occasion, the Mo atom/amine (molar ratio) was 1.05. Then, the reaction mixture was aged at 80° C. for 2 hours and at 110° C. for 1 hour. After completion, unreacted molybdenum trioxide was removed by filtration, and the solvent was removed by vacuum distillation and vacuum drying to obtain 4.34 g of deep green solid friction-reducing agent (A-6). The molybdenum content in the friction-reducing agent (A-6) was 6.4 wt %.

Using the obtained friction-reducing agent (A-6), oil solubility and friction properties were evaluated, and the results are shown in Table 2. The friction-reducing agent (A-6) was excellent in oil solubility, had a low coefficient of friction and had favorable friction-reducing properties.

Example 7

Into a 1 L four-necked flask equipped with a stirring machine and a condenser tube, 19.0 g (0.12 mol) of 3-(1-piperazinyl)-1,2-propanediol, 16.7 g (0.04 mol) of 1-bromo-2-decyl-tetradecane, isopropanol (200 g) and 4.45 g (0.042 mol) of sodium carbonate were added, followed by heating at 90° C. for 8 hours in a stream of nitrogen. After completion of heating, sodium carbonate was removed by filtration, and 2-propanol was removed by vacuum distillation. Then, only the oil layer was collected by extraction with chloroform, which was subjected to vacuum distillation and vacuum drying to obtain 18.9 g (yield: 95.1%) of pale yellow oil 3-(4-(2-decyltetradecyl)-1-piperazinyl)-1,2-propanediol.

Identification was conducted from the results of $^1$H-NMR measurement, $^{13}$C-NMR measurement and elemental analysis.

$^1$H-NMR (CDCl$_3$): 3.68-3.84 (m, 2H), 3.48-3.53 (dd, 1H), 2.11-2.65 (m, 12H), 1.48 (s, 1H), 1.19-1.26 (m, 40H), 0.86-0.90 (t, 6H) [ppm].

$^{13}$C-NMR (CDCl$_3$): 67.19, 65.34, 63.63, 60.81, 53.90, 35.04, 32.60, 32.18, 30.36, 29.96, 29.92, 29.62, 26.84, 22.94, 14.37 [ppm].

Elemental analysis (calculated value): C=74.9, H=13.0, N=5.6,

Elemental analysis (measured value): C=75.0, H=13.4, N=5.7.

Then, into a 100 mL round bottom flask, 4.97 g of 3-(4-(2-decyltetradecyl)-1-piperazinyl)-1,2-propanediol and 12 g of toluene were added, followed by heating at 80° C. for dissolution, and an aqueous molybdenum dispersion having 1.44 g of molybdenum trioxide dispersed in 12 g of water was dropwise added. On that occasion, the Mo atom/amine (molar ratio) was 1.05. Then, the reaction mixture was aged at 80° C. for 2 hours and at 110° C. for 1 hour. After completion, unreacted molybdenum trioxide was removed by filtration, and the solvent was removed by vacuum distillation and vacuum drying to obtain 6.23 g of a deep green solid friction-reducing agent (A-7). The molybdenum content in the friction-reducing agent (A-7) was 12.7 wt %.

Using the obtained friction-reducing agent (A-7), oil solubility and friction properties were evaluated, and the results are shown in Table 2. The friction-reducing agent (A-7) was excellent in oil solubility, had a low coefficient of friction and had favorable friction-reducing properties.

Example 8

Into a 100 mL round bottom flask, 4.97 g of 3-(4-(2-decyltetradecyl)-1-piperazinyl)-1,2-propanediol prepared in Example 7 and 12 g of toluene were added, followed by heating at 80° C. for dissolution, and an aqueous molybdenum dispersion having 0.96 g of molybdenum trioxide dispersed in 12 g of water was dropwise added. On that occasion, the Mo atom/amine (molar ratio) was 0.75. Then, the reaction mixture was aged at 80° C. for 2 hours and at 110° C. for 1 hour. After completion, unreacted molybdenum trioxide was removed by filtration, and the solvent was removed by vacuum distillation and vacuum drying to obtain 5.45 g of a deep green solid friction-reducing agent (A-8). The molybdenum content in the friction-reducing agent (A-8) was 8.8 wt %.

Using the obtained friction-reducing agent (A-8), oil solubility and friction properties were evaluated, and the results are shown in Table 2. The friction-reducing agent (A-8) was excellent in oil solubility, had a low coefficient of friction and had favorable friction-reducing properties.

Example 9

Into a 1 L four-necked flask equipped with a stirring machine and a condenser tube, 70.9 g (0.20 mol) of 2-decyl-1-tetradecanol, 22.3 g (0.22 mol) of triethylamine and 1,320 g of dichloromethane were added, 25.2 g (0.22 mol) of methanesulfonyl chloride was dropwise added in a stream of nitrogen in a state cooled to −10° C. to 0° C., and the reaction mixture was aged at from −10 to 0° C. for 30 minutes and at 25° C. for 17 hours. Then, extraction with a saturated salt solution and removal of the solvent were carried out to obtain 93.0 g of an intermediate.

Then, into a 1 L four-necked flask equipped with a stirring machine and a condenser tube, 92.6 g of the intermediate, 124.4 g (0.54 mol) of 3-(1-piperazinyl)-1,2-propanediol and 150 g of ethanol were added, followed by reaction at 150° C. for 13 hours in a stream of nitrogen. Then, only the oil layer was collected by extraction with chloroform, which was subjected to vacuum distillation and vacuum drying to obtain 81.8 g (yield: 94.0%) of pale yellow oil 3-(4-(2-decyltetradecyl)-1-piperazinyl)-1,2-propanediol.

Identification was conducted from the results of $^1$H-NMR measurement, $^{13}$C-NMR measurement and elemental analysis.

$^1$H-NMR (CDCl$_3$): 3.71-3.82 (m, 2H), 3.50-3.53 (dd, 1H), 2.12-2.66 (m, 12H), 1.48 (s, 1H), 1.20-1.26 (m, 40H), 0.86-0.90 (t, 6H) [ppm].

13C-NMR (CDCl$_3$): 66.76, 65.04, 63.40, 60.37, 53.71, 34.82, 32.37, 31.94, 30.11, 29.72, 29.69, 29.38, 26.61, 22.70, 14.13 [ppm].

Elemental analysis (calculated value): C=74.9, H=13.0, N=5.6,

Elemental analysis (measured value): C=75.0, H=13.1, N=5.7.

Then, into a 100 mL round bottom flask, 9.94 g of 3-(4-(2-decyltetradecyl)-1-piperazinyl)-1,2-propanediol and 25 g of toluene were added, followed by heating at 80° C. for dissolution, and an aqueous molybdenum dispersion having 3.02 g of molybdenum trioxide dispersed in 25 g of water was dropwise added. On that occasion, the Mo atom/amine (molar ratio) was 1.05. Then, the reaction mixture was aged at 110° C. for 1 hour. After completion, unreacted molybdenum trioxide was removed by filtration, and the solvent was removed by vacuum distillation and vacuum drying to obtain 11.5 g of a deep green solid friction-reducing agent (A-9). The molybdenum content in the friction-reducing agent (A-9) was 14.0 wt %.

The friction-reducing agent (A-9) was blended with base oil (C-1) so that the molybdenum concentration would be 500 ppm, and tris(dimethylamino)borane as a boron compound was blended at a concentration of 0.1 wt %, and further, zinc dialkyldithiophosphate (ZnDTP, manufactured by ADEKA CORPORATION, KIKU-LUBE Z-112) as an abrasion inhibitor was blended so that the zinc concentration would be 1,000 ppm, to prepare a blended oil. Using the obtained blended oil, oil solubility and low temperature friction properties were evaluated. The results are shown in Table 3.

The obtained blended oil was excellent in oil solubility, had a low coefficient of friction and had favorable low temperature friction properties.

TABLE 3

| | | Example 9 | Example 10 | Example 11 |
|---|---|---|---|---|
| Friction-reducing agent | A-9 | A-9 | A-9 |
| Amine | Name | 3-(4-(2-decyltetradecyl)-1-piperazinyl)-1,2-propanediol | 3-(4-(2-decyltetradecyl)-1-piperazinyl)-1,2-propanediol | 3-(4-(2-decyltetradecyl)-1-piperazinyl)-1,2-propanediol |
| | Structural formula | (structure shown) | (structure shown) | (structure shown) |
| Molybdenum | | MoO$_3$ | MoO$_3$ | MoO$_3$ |
| Mo/amine (molar ratio) | | 1.05 | 1.05 | 1.05 |
| Mo content (wt %) | | 14.0 | 14.0 | 14.0 |
| Boron compound | Name | Tris(dimethylamino)borane | Tris(dimethylamino)borane | Tris(dimethylamino)borane |
| | Amount blended [wt %] | 0.10 | 0.50 | 1.0 |
| Oil solubility | Results | Soluble | Soluble | Soluble |
| | Evaluation | A | A | A |
| Low temperature Friction properties | Coefficient of friction | 0.070 | 0.071 | 0.070 |
| | Evaluation | A | A | A |

Example 10

A blended oil was prepared in the same manner as in Example 9 except that the amount of tris(dimethylamino)borane as a boron compound blended was 0.5 wt %, and oil solubility and low temperature friction properties were evaluated. The results are shown in Table 3.

The obtained blended oil was excellent in oil solubility, had a low coefficient of friction and had favorable low temperature friction properties.

Example 11

A blended oil was prepared in the same manner as in Example 9 except that the amount of tris(dimethylamino)borane as a boron compound blended was 1.0 wt %, and oil solubility and low temperature friction properties were evaluated. The results are shown in Table 3.

The obtained blended oil was excellent in oil solubility, had a low coefficient of friction and had favorable low temperature friction properties.

Comparative Example 1

Using friction-reducing agent (B-1) comprising base oil (C-1) and zinc dialkyldithiophosphate (ZnDTP, manufactured by ADEKA CORPORATION, KIKU-LUBE Z-112) as an abrasion inhibitor blended so that the zinc concentration would be 1,000 ppm, oil solubility and friction properties were evaluated, and the results are shown in Table 4. The friction-reducing agent (B-1) had a high coefficient of friction and was inferior in friction-reducing properties.

TABLE 4

|  |  | Comparative Example 1 | Comparative Example 2 | Comparative Example 3 | Comparative Example 4 |
|---|---|---|---|---|---|
| Friction-reducing agent | | B-1 | B-2 | B-3 | B-4 |
| Amine | Name | — | 3-(1-piperazinyl)-1,2-propanediol | 2,2',-(dodecylimino)bisethanol | Molybdenum oxysulfide dithiocarbamate |
| | Structural formula | — | (piperazine with propanediol) | (dodecylimino bisethanol) | — |
| Molybdenum | | — | — | $MoO_3$ | — |
| Mo/amine (molar ratio) | | — | — | 1.05 | — |
| Mo content (wt %) | | — | — | 19.3 | 10.0 |
| Oil solubility | Results | Soluble | Separated | Suspended | Soluble |
| | Evaluation | A | C | B | A |
| Friction properties | Coefficient of friction | 0.156 | Evaluation impossible | 0.131 | 0.101 |
| | Evaluation | C | C | C | C |

Comparative Example 2

Using friction-reducing agent (B-2) comprising base oil (C-1) and 3-(1-piperazinyl)-1,2-propanediol blended at a concentration of 0.1 wt %, oil solubility and friction properties were evaluated, and the results are shown in Table 4. The friction-reducing agent (B-2) was inferior in oil solubility and was separated from the base oil, and the friction properties could not be evaluated.

Comparative Example 3

Into a 100 mL round bottom flask, 3.42 g of 2,2'-(dodecylimino)bis-ethanol and 15 g of toluene were added, followed by heating at 80° C. for dissolution, and an aqueous molybdenum dispersion having 1.89 g of molybdenum trioxide dispersed in 15 g of water was dropwise added. On that occasion, the Mo atom/amine (molar ratio) was 1.05. Then, the reaction mixture was aged at 80° C. for 2 hours and at 110° C. for 1 hour. After completion, unreacted molybdenum trioxide was removed by filtration, and the solvent was removed by vacuum distillation and vacuum drying to obtain 3.63 g of deep green solid friction-reducing agent (B-3). The molybdenum content in the friction-reducing agent (B-3) was 19.3 wt %.

Using the obtained friction-reducing agent (B-3), oil solubility and friction properties were evaluated, and the results are shown in Table 4. The friction-reducing agent (B-3) was suspended in the base oil, had a high coefficient of friction and was inferior in friction-reducing properties.

Comparative Example 4

Using friction-reducing agent (B-4) comprising base oil (C-1) and molybdenum oxysulfide dithiocarbamate (MoDTC, manufactured by ADEKA CORPORATION, SAKURA-LUBE 525, Mo content: 10.0 wt %) blended so that the molybdenum concentration would be 500 ppm, oil solubility and friction properties were evaluated, and the results are shown in Table 4. The friction-reducing agent (B-4) had a high coefficient of friction and was inferior in friction-reducing properties.

The present invention was described in detail with reference to specific embodiments, however, it is obvious for the person skilled in the art that various changes and modifications are possible without departing from the intention and the scope of the present invention.

INDUSTRIAL APPLICABILITY

The friction-reducing agent of the present invention is excellent in friction-reducing properties and is thereby suitable as an additive for a lubricating oil. It is particularly useful as an additive for a gasoline engine oil, a Diesel engine oil, a jet engine oil and a gear oil.

The invention claimed is:

1. A method for producing an alkanolamine represented by the following formula (1):

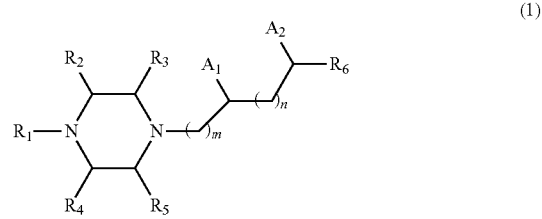

(1)

wherein $A_1$ and $A_2$ are hydroxy groups, $R_1$ is a hydrocarbon group having at least 8 and at most 24 carbon atoms, $R_2$ to $R_6$ are hydrogen atoms, and m is 1 and n is 0, the method comprising reacting a raw material amine represented by the following formula with a halide represented by the following formula or an epoxy compound represented by the following formula and further with a halide represented by the following formula:

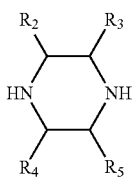

(2)

wherein $R_2$ to $R_5$ are hydrogen atoms;

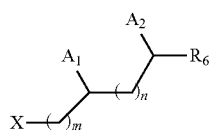

(3)

wherein $A_1$ and $A_2$ are hydroxy groups, $R_6$ is a hydrogen atom, X is a halogen atom, and m is 1 and n is 0;

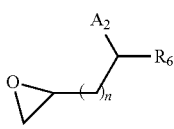

(4)

wherein $A_2$ is a hydroxy group, $R_6$ is a hydrogen atom, and n is 0;

$R_1$—X  (5)

wherein $R_1$ is a hydrocarbon group having at least 8 and at most 24 carbon atoms, and X is a halogen atom.

2. A method for producing an alkanolamine represented by the following formula (1):

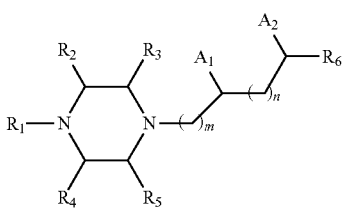

(1)

wherein $A_1$ and $A_2$ are hydroxy groups, $R_1$ is a hydrocarbon group having at least 8 and at most 24 carbon atoms, $R_2$ to $R_6$ are hydrogen atoms, and m is 1 and n is 0, the method comprising reacting a raw material amine represented by the following formula with a halide represented by the following formula and further with a halide represented by the following formula or an epoxy compound represented by the following formula:

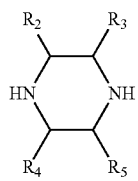

(2)

wherein $R_2$ to $R_5$ are hydrogen atoms;

$R_1$—X  (5)

wherein $R_1$ is a hydrocarbon group having at least 8 and at most 24 carbon atoms, and X is a halogen atom;

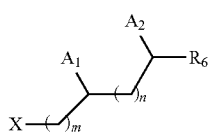

(3)

wherein $A_1$ and $A_2$ are hydroxy groups, $R_6$ is a hydrogen atom, X is a halogen atom, and m is 1 and n is 0;

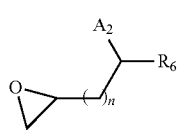

(4)

wherein $A_2$ is a hydroxy group, $R_6$ is a hydrogen atom, and n is 0.

* * * * *